United States Patent
Panken et al.

(10) Patent No.: US 11,033,742 B2
(45) Date of Patent: Jun. 15, 2021

(54) PROBABILISTIC ENTROPY FOR DETECTION OF PERIODIC SIGNAL ARTIFACTS

(71) Applicant: Medtronic, Inc., Minneapolis, MN (US)

(72) Inventors: Eric J. Panken, Edina, MN (US);
Jadin C. Jackson, Roseville, MN (US);
Yizi Xiao, Eden Prairie, MN (US);
Christopher L. Pulliam, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 72 days.

(21) Appl. No.: 16/392,129

(22) Filed: Apr. 23, 2019

(65) Prior Publication Data

US 2020/0338350 A1 Oct. 29, 2020

(51) Int. Cl.
*A61F 9/008* (2006.01)
*A61N 1/36* (2006.01)
(Continued)

(52) U.S. Cl.
CPC .......... *A61N 1/36135* (2013.01); *A61B 5/291* (2021.01); *A61B 5/7221* (2013.01);
(Continued)

(58) Field of Classification Search
CPC .............. A61N 1/36135; A61N 1/0534; A61N 1/0551; A61N 1/37235; A61B 5/0478; A61B 5/7221; A61B 5/7264
See application file for complete search history.

(56) References Cited

U.S. PATENT DOCUMENTS 8,050,751 B2   11/2011  Zhang et al.
8,442,294 B2    5/2013  Sonke et al.
(Continued)

FOREIGN PATENT DOCUMENTS

CN    106512206       3/2017
EP     2453792 B1     5/2017

OTHER PUBLICATIONS

Islam, "Artifact Characterization, Detection, and Removal from Neural Signals," Department of Electrical and Computer Engineering National University of Singapore, Jul. 2015, 276 pp.
(Continued)

*Primary Examiner* — Michael W Kahelin
*Assistant Examiner* — George E Banis
(74) *Attorney, Agent, or Firm* — Shumaker & Sieffert, P.A.

(57) ABSTRACT

Techniques are disclosed for using probabilistic entropy to select electrodes with fewer artifacts for controlling adaptive electrical neurostimulation. In one example, a plurality of electrodes sense bioelectrical signals of a brain of a patient. Processing circuitry determines, for each bioelectrical signal sensed at a respective electrode of the plurality of electrodes, a probabilistic entropy value of the bioelectrical signal. The processing circuitry compares each of the respective probabilistic entropy values of the bioelectrical signal to respective entropy threshold values and selects, based on the comparisons, a subset of electrodes of the plurality of electrodes. The processing circuitry controls, based on the bioelectrical signals sensed via respective electrodes of the subset of electrodes and excluding the bioelectrical signals of the plurality of bioelectrical signals sensed via respective electrodes not in the subset of electrodes, delivery of electrical stimulation therapy to the patient.

26 Claims, 8 Drawing Sheets

(51) Int. Cl.
  *A61B 5/00*   (2006.01)
  *A61N 1/05*   (2006.01)
  *A61N 1/372*  (2006.01)
  *A61B 5/291*  (2021.01)

(52) U.S. Cl.
  CPC .......... *A61B 5/7264* (2013.01); *A61N 1/0534* (2013.01); *A61N 1/0551* (2013.01); *A61N 1/37235* (2013.01)

(56) References Cited

U.S. PATENT DOCUMENTS

| | | | |
|---|---|---|---|
| 8,718,753 B2 | 5/2014 | Chon et al. | |
| 9,408,575 B2 | 8/2016 | Bordoley et al. | |
| 2007/0135727 A1 | 6/2007 | Virtanen et al. | |
| 2008/0195166 A1* | 8/2008 | Sun ..................... | A61B 5/4815 607/18 |
| 2012/0245481 A1* | 9/2012 | Blanco ................ | A61B 5/7264 600/544 |
| 2016/0045128 A1* | 2/2016 | Sitt ..................... | A61B 5/0075 600/409 |
| 2016/0228705 A1* | 8/2016 | Crowder ............... | A61B 5/048 |
| 2018/0071530 A1 | 3/2018 | Giftakis et al. | |

OTHER PUBLICATIONS

Richman et al., "Physiological time-series analysis using approximate entropy and sample entropy," Am J Physiol Heart Circ Physiol, 278, Jun. 1, 2000, 11 pp.
Mariani et al., "Use of Multiscale Entropy to Facilitate Artifact Detection in Electroencephalographic Signals," ISBN 978-1-4244-9270-1, IEEE, Nov. 5, 2015, 4 pp.
Skupch et al., "EEG Artifact Detection Using Spatial Distribution of Rhythmicity," ICBET 2013, May 19-20, 2013, Elsevier, 5 pp.
International Search Report and Written Opinion of International Application No. PCT/US2020-028795, dated Jul. 2, 2020, 15 pp.

* cited by examiner

PROBABILISTIC ENTROPY FOR DETECTION OF PERIODIC SIGNAL ARTIFACTS

FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patent. Hence, electrical stimulation may be used in different therapeutic applications, such as adaptive deep brain stimulation (aDBS), spinal cord stimulation (SCS), pelvic stimulation, gastric stimulation, peripheral nerve field stimulation (PNFS), electroencephalography (EEG), electrocorticography (ECoG), electromyography (EMG), or for performing bio-potential recording of other channels of a patient.

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, and a pulse frequency as stimulation parameters. A set of parameters, such as a set including electrode combination, electrode polarity, amplitude, pulse width, and pulse rate, may be referred to as a program in the sense that the define the electrical stimulation therapy to be delivered to the patient.

SUMMARY

Bioelectrical signals sensed from a patient, such as local field potentials (LFP), EEG, ECoG, or EMG, may be used as biomarkers or input signals for control systems for therapy delivery, such as aDBS. For example, LFP signals may be used as biomarkers for controlling one or more parameters of electrical stimulation therapy delivered to a patient. However, the clinical usefulness of recorded bioelectrical signals may be compromised if the recorded bioelectrical signals are contaminated with artifacts. A variety of factors, such as electrocardiogram (ECG) signals or repetitive motion, may distort the recorded bioelectrical signals or introduce artifacts in the recorded bioelectrical signals. The amplitudes of these artifacts are often variable across recordings, and therefore, medical devices may be limited in detecting the artifacts via conventional algorithms. However, the artifacts may be periodic in nature (e.g., heartbeat, pacing therapy), and the periodicity may be exploited for building detection algorithms. Periodicity, as used herein, refers to pattern or order in the signal, which has lower entropy (e.g., randomness) than bioelectrical signals such as neuronal LFP activity, which may exhibit more stochastic (e.g., random) properties. Therefore, the entropy of one or more features of a recorded bioelectrical signal can be used as a salient feature to identify periodic artifacts.

Techniques are disclosed for using probabilistic entropy to differentiate electrodes capable of sensing clean bioelectrical signals from electrodes contaminated with artifacts. In some examples, the techniques may be used to verify that a bioelectrical signal sensed by recording electrodes is of a sufficient quality for use as a biomarker in controlling aDBS therapy. In some examples, the probabilistic entropy may be used as an indicator of periodic artifacts, such as ECG, that are present in recorded LFP signals of a brain of a patient. In one example, a plurality of electrodes sense bioelectrical signals of the brain of the patient. Processing circuitry determines, for each bioelectrical signal sensed at a respective electrode of the plurality of electrodes, a probabilistic entropy value of the bioelectrical signal. The processing circuitry compares each of the respective probabilistic entropy values of the bioelectrical signal to respective entropy threshold values and selects, based on the comparisons, a subset of electrodes of the plurality of electrodes. Thus, the processing circuitry may use the probabilistic entropy value of the bioelectrical signal to improve the selection of electrodes that are used for sensing bioelectrical signals of the patient or for delivering therapy to the patient. For example, the processing circuitry controls, based on the bioelectrical signals sensed via respective electrodes of the subset of electrodes and excluding the bioelectrical signals of the plurality of bioelectrical signals sensed via respective electrodes not in the subset of electrodes, delivery of electrical stimulation therapy to the patient. As another example, the processing circuitry senses, based on the bioelectrical signals sensed via respective electrodes of the subset of electrodes and excluding the bioelectrical signals of the plurality of bioelectrical signals sensed via respective electrodes not in the subset of electrodes, one or more bioelectrical signals of the patient.

Accordingly, the techniques disclosed herein may provide enhanced accuracy in the identification of artifacts in electrodes. For example, the techniques of the disclosure may detect artifacts that may otherwise be difficult to detect using conventional artifact detection methods, such as artifacts that have variable signal amplitudes across multiple recordings. Thus, by identifying and eliminating measurements from electrodes that are contaminated with artifacts, the techniques of the disclosure may provide higher reliability in aDBS systems. For example, the techniques of the disclosure may increase the likelihood that signals sensed by the electrodes and used as biomarkers for aDBS accurately reflect the true bioelectrical signal and avoid erroneous measurements which may adversely affect the therapy provided to the patient. Therefore, the techniques disclosed herein may provide aDBS therapy to a patient that is more effective than conventional systems.

In one example, this disclosure describes a method comprising: sensing, via a plurality of electrodes, a plurality of bioelectrical signals of a brain of a patient; determining, by processing circuitry and for each bioelectrical signal of the plurality of bioelectrical signals sensed at a respective electrode of the plurality of electrodes, a probabilistic entropy value of the bioelectrical signal; comparing, by the processing circuitry, each of the respective probabilistic entropy values of the bioelectrical signal to respective entropy threshold values; and selecting, by the processing circuitry and based on the comparisons, a subset of electrodes of the plurality of electrodes; and controlling, by the processing circuitry and based on the bioelectrical signals of the plurality of bioelectrical signals sensed via respective electrodes of the subset of electrodes and excluding the bioelectrical signals of the plurality of bioelectrical signals sensed via respective electrodes not in the subset of electrodes, delivery of electrical stimulation therapy to the patient.

In another example, this disclosure describes an implantable medical device comprising: a plurality of electrodes; sensing circuitry configured to sense, via the plurality of electrodes, a plurality of bioelectrical signals of a brain of a patient; and processing circuitry configured to: determine, for each bioelectrical signal of the plurality of bioelectrical signals sensed at a respective electrode of the plurality of electrodes, a probabilistic entropy value of the bioelectrical signal; compare each of the respective probabilistic entropy values of the bioelectrical signal to respective entropy threshold values; select, based on the comparisons, a subset of electrodes of the plurality of electrodes; and control, based on the bioelectrical signals of the plurality of bioelectrical signals sensed via respective electrodes of the subset of electrodes and excluding the bioelectrical signals of the plurality of bioelectrical signals sensed via respective electrodes not in the subset of electrodes, delivery of electrical stimulation therapy to the patient.

In another example, this disclosure describes a system comprising: an implantable medical device comprising: a plurality of electrodes; sensing circuitry configured to sense, via the plurality of electrodes, a plurality of bioelectrical signals of a brain of a patient; and processing circuitry configured to: determine, for each bioelectrical signal of the plurality of bioelectrical signals sensed at a respective electrode of the plurality of electrodes, a probabilistic entropy value of the bioelectrical signal; compare each of the respective probabilistic entropy values of the bioelectrical signal to respective entropy threshold values; select, based on the comparisons, a subset of electrodes of the plurality of electrodes; and control, based on the bioelectrical signals of the plurality of bioelectrical signals sensed via respective electrodes of the subset of electrodes and excluding the bioelectrical signals of the plurality of bioelectrical signals sensed via respective electrodes not in the subset of electrodes, delivery of a therapy such as electrical stimulation therapy, to the patient.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
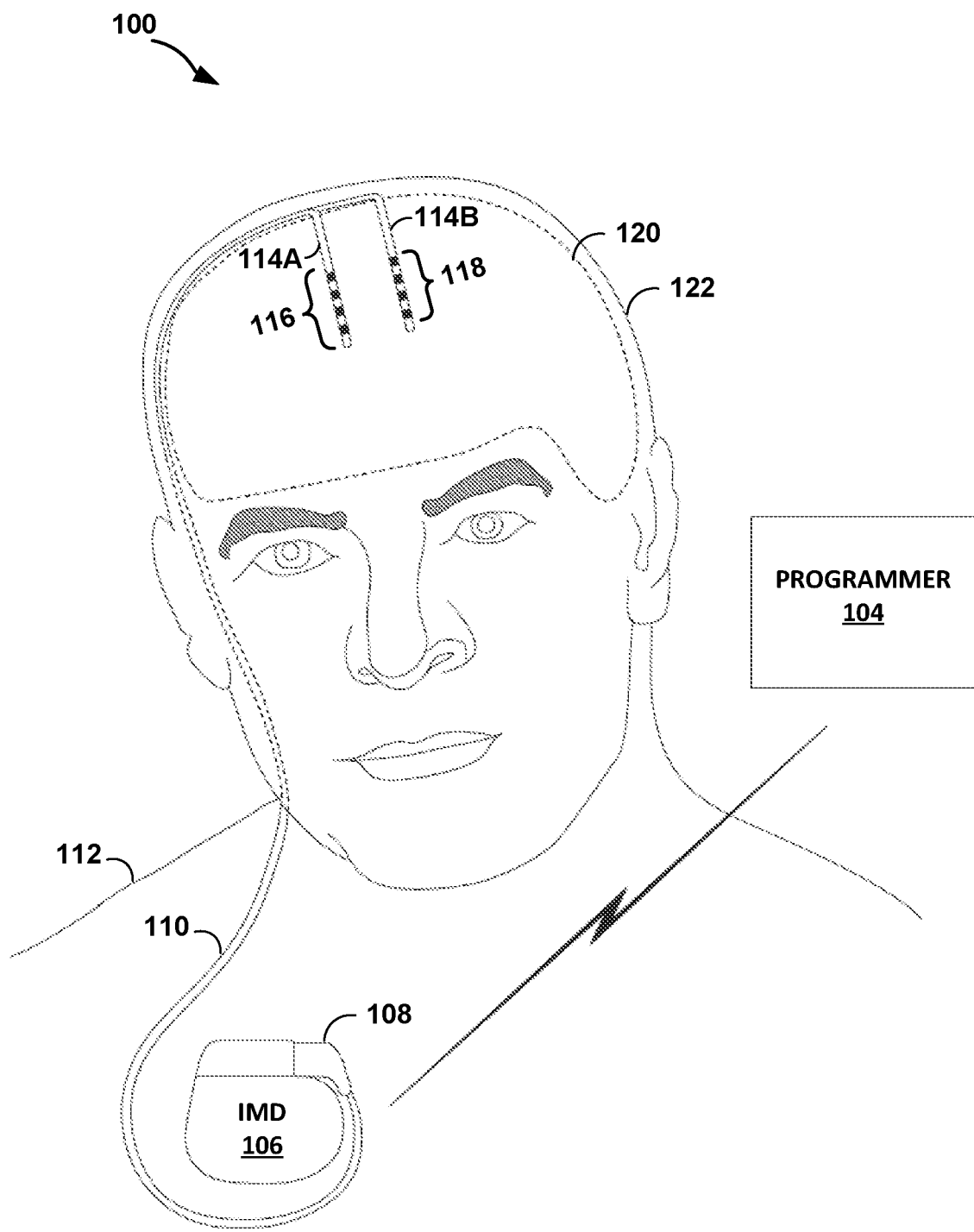
FIG. 1 is a conceptual diagram illustrating an example system that includes an implantable medical device (IMD) configured to deliver adaptive DBS to a patient according to an example of the techniques of the disclosure.

FIG. 1 is a conceptual diagram illustrating an example system 100 that includes an implantable medical device (IMD) 106 configured to deliver adaptive deep brain stimulation to a patient 112. DBS may be adaptive in the sense that IMD 106 may adjust, increase, or decrease the magnitude of one or more parameters of the DBS in response to changes in patient activity or movement, a severity of one or more symptoms of a disease of the patient, a presence of one or more side effects due to the DBS, or one or more sensed bioelectrical signals of the patient, etc. For example, one or more sensed signals of the patient may be used as a control signal such that the IMD 106 correlates the magnitude of the one or more parameters of the electrical stimulation to the magnitude of one or more features of the one or more sensed bioelectrical signals. IMD 106 may deliver electrical stimulation therapy having one or more parameters, such as voltage or current amplitude, adjusted in response to the magnitude of the one or more features of the one or more sensed bioelectrical signals.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, pain, spasticity, incontinence, dysthymic disorder, and obsessive-compulsive disorder (OCD)). At least some of these disorders may be manifested in one or more patient movement behaviors. As described herein, a movement disorder or other neurological impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

In the example of FIG. 1, system 100 is described as a DBS system. However, the techniques disclosed herein may be applied to other types of therapy systems for managing patient symptoms that are not expressly illustrated in the example of FIG. 1. For example, the techniques of the disclosure described herein may additionally be applied to systems that delivery spinal cord stimulation (SCS) therapy for spinal cord injury or to suppress pain in patient 112. Further, the techniques of the disclosure may be applied to a system that delivers pelvic stimulation (e.g., sacral neural modulation) to delivery therapy for pelvic health and/or gastronomic applications.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense bioelectrical signals within brain 120 of patient 112. In some examples, some of electrodes 116, 118 may be configured to sense bioelectrical signals and others of electrodes 116, 118 may be configured to deliver adaptive electrical stimulation to brain 120. In other examples, all of electrodes 116, 118 are configured to both sense bioelectrical signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the bioelectrical signals sensed within brain 120 may reflect changes in electrical current produced by the sum of electrical potential differences across brain tissue. Examples of bioelectrical signals include, but are not limited to, electrical signals generated from local field potentials (LFP) sensed within one or more regions of brain 120, such as an electroencephalogram (EEG) signal, an electrocorticogram (ECoG) signal, or other types of neurological brain signals. Local field potentials, however, may include a broader genus of electrical signals within brain 120 of patient 112.

In some examples, the bioelectrical signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing bioelectrical signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a selected therapy program. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes.

IMD 106 may be implanted within a subcutaneous pocket above the clavicle, or, alternatively, on or within cranium 122, within the abdomen of patient 112, or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Leads 114 may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex or less complex lead array geometries and/or electrode array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114. Leads 114 may also be placed elsewhere within the central or peripheral nervous system as required to sense or modulate nervous system activity. In other examples not depicted in the example of FIG. 1, leads 114 may be implanted in other locations of patient 112, such as proximate to a spinal cord, a sacral nerve, or a muscle fiber (e.g., for EMG).

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder. In some examples, the therapy program may be stored on another device, such as external programmer 104 or distributed across one or more computing devices (e.g., a cloud computing system).

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114). Programmer 104 may also be capable of downloading or streaming patient data from IMD 106 and processing such patient data. In some examples, programmer 104 may download and process such patient data immediately or on a delayed or periodic basis. In other examples, programmer 104 may upload such patient data to one or more computing devices (e.g., a cloud computing network) for processing. In some examples, programmer 104 may upload such patient data immediately or on a delayed or periodic basis.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., one or more features of one or more bioelectrical signals, muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter. As is described in more detail below, in some examples, programmer 104 displays, to a clinician or patient, a notification that an artifact is present in one or more electrodes 116, 118 of leads 114.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 104 is described as delivering electrical stimulation therapy to brain 120, IMD 106 may be configured to direct electrical stimulation to other anatomical regions of patient 112. In other examples, system 100 may include an implantable drug pump in addition to, or in place of, IMD 106. Further, an IMD may provide other electrical stimulation such as, e.g., spinal cord stimulation to treat a movement disorder.

According to the techniques of the disclosure, system 100 may sense a bioelectrical signal of brain 120 of patient 112 via electrodes 116, 118 and determine a probabilistic entropy of the bioelectrical signal. System 100 may use the probabilistic entropy of the bioelectrical signal to differentiate electrodes of electrodes 116, 118 that are capable of sensing clean bioelectrical signals from electrodes of electrodes 116, 118 that are contaminated with artifacts. Bioelectrical signals in brain 120 of patient 112, such as neuronal LFP activity, may typically exhibit stochastic (e.g., random) behavior and exhibit high entropy. In contrast, pattern or order in a sensed bioelectrical signal exhibits low entropy. Low entropy in the sensed signal may be indicative of artifacts in the sensed signal, such as periodic artifacts occurring due to ECG, movement, or other sources of periodic noise. In other words, if a sensed signal exhibits random behavior (e.g., stochastic process), and therefore, high entropy, the sensed signal tends to not include artifacts. However, if the sensed signal exhibits periodic components (e.g., patterns or high order), and therefore, low entropy, the sensed signal may include artifacts.

In some examples, system 100 derives the probabilistic entropy value of the bioelectrical signal from a probability distribution of values of the bioelectrical signal over a period of time. For example, b[i] may represent a histogram of measurements of values of the bioelectrical signal over a period of time, and f[i] may represent a fraction of the values of the bioelectrical signal in b[i] (e.g., the number of "slices" or "segments" of the histogram b[i]). This can, for example, be computed using the Shannon entropy from the histogram of values. For example, let f[i] equal the fraction of values in b[i]. Then, the Shannon entropy is defined by the following equation:

$$\text{Shannon Entropy} = -\text{sum}(f[i]*\log_2(f[i])), \text{ for } f[i] > 0.$$

A uniform distribution of values indicates high entropy in the sensed bioelectrical signal, such as may be the case for a white noise signal. In contrast, a non-uniform distribution of values indicates low entropy in the sensed bioelectrical signal, such as may be the case for a signal that includes a periodic or sinusoidal component. The techniques of the disclosure recognize that low-entropy signals that include periodic or sinusoidal components may include artifacts that contaminate the signal, while high-entropy signals may not include such periodic or sinusoidal components and may more accurately represent the random, high-entropy bioelectrical signals of brain 120 of patient 112.

For instance, a non-uniform distribution may occur for a sensed bioelectrical signal that includes a periodic or sinusoidal component. Because the probability distribution of values of a periodic signal exhibits a constrained frequency spectrum, the spectral power of a periodic signal may exhibit higher order and less entropy than, e.g., white noise signal (e.g., a signal that is random or exhibits high entropy). Periodic signals have a constrained frequency spectrum so, based on spectral power, an entropy of a periodic signal is lower than, e.g., an entropy of a white noise spectrum. In this example, the entropy value of the periodic signal may be relatively low because there is order or pattern in the signal. In some cases, a strong pattern may be indicative of the existence of a desirable signal (e.g., a desired component of a sensed signal, such as an LFP recording from patient 112). In other cases, such strong periodicity may indicate the presence of an undesirable signal source (e.g., a component of the sensed signal that is due to unwanted noise). For example, if a sensed signal includes a component exhibiting strong periodicity in a frequency spectrum outside of a frequency spectrum of a biomarker of neuronal activity, system 100 may classify the sensed signal as contaminated with artifacts.

In contrast, an even or broad distribution of values may arise where the bioelectrical signal exhibits high entropy. For example, if the probability distribution values of spectral power are relatively evenly spread out (e.g., no one component of the sensed signal is any more probable than any other value), as is the case for many bioelectrical signals, the sensed signal may not have a dominant periodic signal component. In this example, the entropy value may be relatively high since there is less order or pattern in the sensed signal. Further, system 100 may classify a signal with such a high entropy value as "clean" e.g., exhibiting few or no artifacts.

In some examples, the probabilistic entropy value of the bioelectrical signal is a statistical measure of randomness of values of the bioelectrical signal over a period of time. Thus, the probabilistic entropy value of the bioelectrical signal is a measure of the level of randomness of the bioelectrical signal. In some examples, system 100 may verify that a bioelectrical signal sensed by one of electrodes 116, 118 is of a sufficient quality for use as a biomarker in controlling aDBS therapy. In some examples, system 100 may use a probabilistic entropy of a bioelectrical signal sensed by one of recording electrodes 116, 118 as an indicator of interference from other periodic bioelectrical signals, such as, ECG or other types of periodic artifacts present in recorded bioelectrical signals of brain 120 of patient 112.

In one example, IMD 106 senses, via electrodes 116, 118, a plurality of bioelectrical signals of brain 120 of patient 112. IMD 106 determines, for each bioelectrical signal sensed at a respective electrode 116, 118, a probabilistic entropy value of the bioelectrical signal. IMD 106 compares each of the respective probabilistic entropy values of the sensed bioelectrical signal to respective entropy threshold values. IMD 106 selects, based on the comparisons, a subset of electrodes 116, 118. IMD 106 controls, based on the bioelectrical signals sensed via respective electrodes of the subset of electrodes 116, 118 and excluding the bioelectrical signals of the plurality of bioelectrical signals sensed via respective electrodes 116, 118 not in the subset, delivery of electrical stimulation therapy to patient 112.

For instance, as described above, in aDBS, IMD 106 may determine the therapy to deliver based at least in part on the sensed bioelectrical signals. If the sensed signals have low entropy, then there is a likelihood that there are artifacts in the sensed signals, and IMD 106 may not be able to completely differentiate between the actual bioelectrical signals and the artifacts. In such examples, IMD 106 may not rely on the sensed signals having the artifacts to determine the therapy to deliver. If the sensed signals have high entropy, then there is a likelihood that the sensed signals are an accurate representation of the patient generated bioelectrical signals, and IMD 106 may rely on the sensed signals to determine the therapy to deliver.

In the foregoing example, the above techniques for differentiating electrodes capable of sensing clean bioelectrical signals from electrodes contaminated with artifacts are performed by IMD 106. However, in other examples of the techniques of the disclosure may be performed by external programmer 104. In further examples, the techniques of the disclosure are performed by one or more computing devices not depicted in FIG. 1 that communicate with IMD 106, such as a laptop, a tablet, a smartphone, a PDA, a cloud computing system, and the like. In still further examples, the techniques of the disclosure may be performed by a combination of any one or more of IMD 106, external programmer 104, or the aforementioned computing devices.

Accordingly, the techniques disclosed herein may provide enhanced accuracy in the identification of artifacts in electrodes. For example, the techniques of the disclosure may detect artifacts that may otherwise be difficult to detect using conventional artifact detection methods, such as artifacts that have variable signal amplitudes across multiple recordings. Thus, by identifying and eliminating measurements from electrodes that are contaminated with artifacts, the techniques of the disclosure may provide higher reliability that signals sensed by the electrodes and used as biomarkers for aDBS accurately reflect the true bioelectrical signal and avoid erroneous measurements which may adversely affect the therapy provided to the patient. Therefore, the techniques disclosed herein may provide aDBS therapy to a patient that is more effective than conventional systems.

Figure 2:
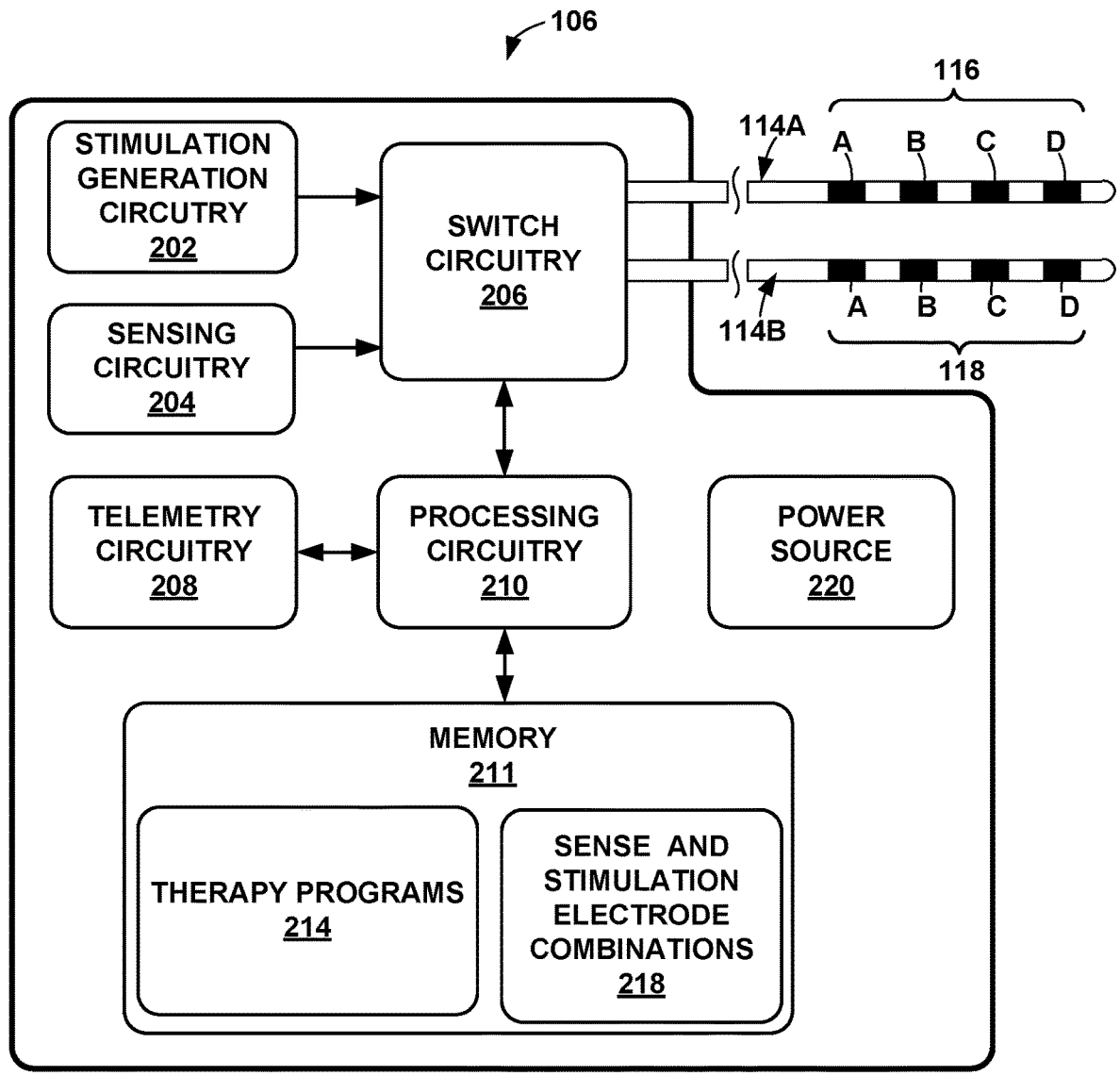
FIG. 2 is a block diagram of the example IMD of FIG. 1 for delivering adaptive DBS therapy according to an example of the techniques of the disclosure.

FIG. 2 is a block diagram of the example IMD 106 of FIG. 1 for delivering adaptive deep brain stimulation therapy. In the example shown in FIG. 2, IMD 106 includes processing circuitry 210, memory 211, stimulation generation circuitry 202, sensing circuitry 204, switch circuitry 206, telemetry circuitry 208, sensor 212, and power source 220. Each of these circuits may be or include electrical circuitry configured to perform the functions attributed to each respective circuit. For example, processing circuitry 210 may include processing circuitry, switch circuitry 206 may include switch circuitry, sensing circuitry 204 may include sensing circuitry, and telemetry circuitry 208 may include telemetry circuitry. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 106 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. As described above, in some examples, sense and stimulation electrode combinations 218 may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processing circuitry 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination.

Stimulation generation circuitry 202, under the control of processing circuitry 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 90 to 170 Hertz or such as approximately 90 Hertz.
2. In the case of a voltage controlled system, Voltage Amplitude: between approximately 0.1 volts and approximately 50 volts, such as between approximately 2 volts and approximately 3 volts.
3. In the alternative case of a current controlled system, Current Amplitude: between approximately 1 milliamps to approximately 3.5 milliamps, such as between approximately 1.0 milliamps and approximately 1.75 milliamps.
4. Pulse Width: between approximately 50 microseconds and approximately 500 microseconds, such as between approximately 50 microseconds and approximately 200 microseconds.

Accordingly, in some examples, stimulation generation circuitry 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs 214 stored in memory 211 to apply particular stimulation parameter values specified by one or more of programs, such as voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls switch circuitry 206 to apply the stimulation signals generated by stimulation generation circuitry 202 to selected combinations of electrodes 116, 118. In particular, switch module 204 may couple stimulation signals to selected conductors within leads 114, which, in turn, deliver the stimulation signals across selected electrodes 116, 118. Switch circuitry 206 may be a switch array, switch matrix, multiplexer, or any other type of switching module configured to selectively couple stimulation energy to selected electrodes 116, 118 and to selectively sense bioelectrical signals with selected electrodes 116, 118. Hence, stimulation generation circuitry 202 is coupled to electrodes 116, 118 via switch circuitry 206 and conductors within leads 114. In some examples, however, IMD 106 does not include switch circuitry 206.

Stimulation generation circuitry 202 may be a single channel or multi-channel stimulation generator. In particular, stimulation generation circuitry 202 may be capable of delivering a single stimulation pulse, multiple stimulation pulses, or a continuous signal at a given time via a single electrode combination or multiple stimulation pulses at a given time via multiple electrode combinations. In some examples, however, stimulation generation circuitry 202 and switch circuitry 206 may be configured to deliver multiple channels on a time-interleaved basis. For example, switch circuitry 206 may serve to time divide the output of stimulation generation circuitry 202 across different electrode combinations at different times to deliver multiple programs or channels of stimulation energy to patient 112. Alternatively, stimulation generation circuitry 202 may comprise multiple voltage or current sources and sinks that are coupled to respective electrodes to drive the electrodes as cathodes or anodes. In this example, IMD 106 may not require the functionality of switch circuitry 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. In one example, the electrodes may be electrically coupled to switch circuitry 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques. Example bioelectrical signals include, but are not limited to, a signal generated from local field potentials (LFPs) within one or more regions of brain 28. EEG and ECoG signals are examples of local field potentials that may be measured within brain 120. However, local field potentials may include a broader genus of electrical or neurological signals within brain 120 of patient 112. Other examples of bioelectrical signals may include signals from a nerve fiber (e.g., a spinal cord) of the patient sensed via EEG or ECoG or a signal from a muscle fiber of the patient sensed via EMG.

Telemetry circuitry 208 supports wireless communication between IMD 106 and an external programmer 104 or another computing device under the control of processing circuitry 210. Processing circuitry 210 of IMD 106 may receive, as updates to programs, values for various stimulation parameters such as magnitude and electrode combination, from programmer 104 via telemetry circuitry 208. The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil or other power transfer mechanism or modality within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

In one example, processing circuitry 210 of IMD 106 senses, via electrodes 116, 118 interposed along leads 114 (and sensing circuitry 202), one or more bioelectrical signals of brain 120 of patient 112. Further, processing circuitry 210 of IMD 106 delivers, via electrodes 116, 118 (and stimulation generation circuitry 202), electrical stimulation therapy to patient 112 based on the sensed one or more bioelectrical signals of brain 120. The adaptive DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers to patient 112 adaptive DBS and may adjust one or more parameters defining the electrical stimulation based on corresponding parameters of the sensed one or more bioelectrical signals of brain 120.

In some examples, processing circuitry 210 continuously measures the one or more bioelectrical signals in real time. In other examples, processing circuitry 210 periodically samples the one or more bioelectrical signals according to a predetermined frequency or after a predetermined amount of time. In some examples, processing circuitry 210 periodically samples the signal at a frequency of approximately 200 Hertz. In some examples, processing circuitry 210 periodically samples the signal at a frequency of approximately 250 Hertz.

According to the techniques of the disclosure, IMD 106 may use the probabilistic entropy of one or more bioelectrical signals of brain 120 of patient 112 sensed via electrodes 116, 118 to differentiate electrodes capable of sensing clean bioelectrical signals from electrodes contaminated with artifacts. The techniques of the disclosure recognize that bioelectrical signals in brain 120 of patient 112, such as neuronal LFP activity, may typically exhibit stochastic (e.g., random) behavior and exhibit high entropy in the spectral component of a recorded signal. In contrast, the techniques of the disclosure recognize that pattern or order in the spectral band power of the sensed bioelectrical signal (e.g., low entropy in the band power), may be indicative of artifacts in the sensed signal, such as artifacts occurring due to ECG, movement, or other types of periodic artifacts. In some examples, IMD 106 may verify that a bioelectrical signal sensed by one of electrodes 116, 118 is of a sufficient quality for use as a biomarker in controlling therapy delivery, such as aDBS therapy. In some examples, IMD 106 may use a probabilistic entropy of a bioelectrical signal sensed by each one of recording electrodes 116, 118 as an indicator of ECG or other periodic artifacts present in recorded LFP signals of brain 120 of patient 112 for that particular electrode of electrodes 116, 118.

In one example, processing circuitry 210 senses, via electrodes 116, 118 and sensing circuitry 204, a plurality of bioelectrical signals of brain 120 of patient 112. Processing circuitry 210 determines, for each bioelectrical signal sensed at a respective electrode 116, 118, a probabilistic entropy value of the bioelectrical signal. Additional examples of how processing circuitry 210 may determine the probabilistic entropy are provided in further detail below. Processing circuitry 210 compares each of the respective probabilistic entropy values of the sensed bioelectrical signal to respective entropy threshold values.

In some examples, the entropy threshold values are defined by a clinician. In some examples, the entropy threshold values are generated by a machine learning model. For example, a machine learning model may be trained with training data comprising a plurality of bioelectrical signals from a plurality of patients, each bioelectrical signal labeled with data indicating whether the bioelectrical signals include one or more artifacts and the location of the one or more artifacts (if present). In some examples, the machine learning model is a supervised learning algorithm that uses training data comprising input features with associated target labels. In some examples, the machine learning model is a logistic regression, support vector machine, random forest, or gradient boosting machine. In some examples, the machine learning model receives one or more features of a sensed bioelectrical signal, such as an entropy of a band power, a threshold crossing rate, and/or an entropy of inter-threshold crossing intervals, as input features. In some examples, inputs are labeled with target labels defining portions of the signal that exhibit artifacts or the absence of artifacts. The machine learning model may process the training data to determine relationships of one or more characteristics of one or more features of the bioelectrical signals to the presence of artifacts in the bioelectrical signals. For example, the machine learning model may determine a correlation of the one or more characteristics of the one or more features of the bioelectrical signals to the presence of artifacts in the bioelectrical signal, as well as a strength of the correlation. In one example, the machine learning model uses one or more of the one or more characteristics of the one or more features of the bioelectrical signal, the correlation of the one or more characteristics to the presence of artifacts in the bioelectrical signal, or the strength of the correlation, as the entropy threshold value.

Further, the machine learning model may iteratively process the training data to determine different weights that correspond to the strength of the correlation of the one or more characteristics of the one or more features of the bioelectrical signal to the presence of artifacts in the bioelectrical signal. In examples described below that use multiple methods to determine the presence of artifacts in a bioelectrical signal, the machine learning model may apply a weight to each respective method so as to more accurately identify the presence of artifacts in the bioelectrical signal.

Processing circuitry 210 may determine the probabilistic entropy value of the bioelectrical signal in a number of ways. As examples, which will be described in more detail below, processing circuitry 210 may determine the probabilistic entropy value of the bioelectrical signal by: 1) analyzing a statistical measure of randomness of spectral power across a plurality of frequency bands of the bioelectrical signal; or 2) comparing an entropy of one or more features of the bioelectrical signal to a threshold limit. However, processing circuitry 210 may determine the probabilistic entropy value of the bioelectrical signal using other methods contemplated by the techniques of the disclosure by not expressly described herein.

Determining the probabilistic entropy value by analyzing a statistical measure of randomness of spectral power across a plurality of frequency bands of the bioelectrical signal.

As one example, processing circuitry 210 may determine the probabilistic entropy value of the bioelectrical signal by analyzing a statistical measure of randomness of spectral power across a plurality of frequency bands of the bioelectrical signal. Processing circuitry 210 divides the bioelectrical signal into a plurality of frequency bands. In some examples, processing circuitry 210 applies Welch's method to determine a spectral power for each frequency band of the bioelectrical signal. In one example, processing circuitry 210 samples an LFP signal in the time domain at a frequency of 250 Hertz and divides the sampled LFP signal into 1 second segments with a 50% overlap. For example, a first segment includes values of the sampled LFP signal from 0 seconds to 1 second, a second segment includes values of the sampled LFP signal from 0.5 seconds to 1.5 seconds, a third segment includes values of the sampled LFP signal from 1 second to 2 seconds, a fourth segment includes values of the sampled LFP signal from 1.5 seconds to 2.5 seconds, etc. Processing circuitry 210 applies a Hanning window to window each segment of the sampled LFP signal. Processing circuitry 210 calculates a periodogram for each 1 second segment of the LFP signal that depicts a power spectral density (PSD) over the 1 second segment. In some examples, the periodogram depicts the square of the magnitude of a Fast Fourier Transform (FFT) of each windowed 1 second segment of the sampled LFP signal. Processing circuitry 210 averages the periodograms to calculate a power spectral density for the sampled LFP signal for each frequency band. Thus, processing circuitry 210 may use the periodograms to empirically determine the statistical distribution of spectral power across each frequency band and can average the periodograms to produce an average power spectral density, namely the distribution of power for each spectral band.

Processing circuitry 210 determines a statistical measure of randomness of the calculated power spectral density across the frequency bands of the sampled LFP signal. As one example, if the calculated power spectral density has a non-uniform distribution of values, the sampled LFP signal demonstrates low entropy and may include a periodic or sinusoidal component. Thus, in this example, the non-uniform distribution of values in the power spectral density of the sampled LFP signal may indicate that the sampled LFP signal includes artifacts that contaminate the signal. For example, processing circuitry 210 compares the statistical measure of randomness of the calculated power spectral density to respective entropy threshold values. If the statistical measure of randomness of the calculated power spectral density is less than an entropy threshold value (which may be the case if a particular band of the sampled LFP signal has a periodic or sinusoidal component), the statistical measure of randomness is indicative of a bioelectrical signal contaminated with artifacts.

In another example, if the calculated power spectral density has a uniform distribution of values, the sampled LFP signal demonstrates high entropy. Thus, in this example, the uniform distribution of values in the power spectral density of the sampled LFP signal may indicate that the sampled LFP signal has no or few artifacts. For example, processing circuitry 210 compares the statistical measure of randomness of the calculated power spectral density to respective entropy threshold values. If the statistical measure of randomness of the calculated power spectral density is greater than an entropy threshold value (which may be the case if no particular frequency band of the sampled LFP signal exhibits greater power density than any other frequency band of the sampled LFP signal), the statistical measure of randomness is indicative of a bioelectrical signal contaminated with no or few artifacts.

In the aforementioned example, processing circuitry 210 determines a statistical measure of randomness of the calculated power spectral density across all bands of the sampled LFP signal to quantify the entropy of the entire sampled LFP signal. However, in other examples, processing circuitry 210 may determine a statistical measure of randomness of the calculated power spectral density of only a portion of the sampled LFP signal. For example, processing circuitry 210 may determine a first statistical measure of randomness of a calculated power spectral density of a first frequency band of the sampled LFP signal and determine a second statistical measure of randomness of a calculated power spectral density of a second frequency band of the sampled LFP signal. In one example, if the first statistical measure of randomness of the power spectral density of the first frequency band indicates that the sampled LFP signal is contaminated with artifacts but the second statistical measure of randomness of the power spectral density of the second frequency band indicates that the sampled LFP signal is clean, processing circuitry 210 determines that the sampled LFP signal is contaminated with artifacts. In another example, processing circuitry 210 determines that the sampled LFP signal is contaminated with artifacts only if both the first and second statistical measures of randomness of the power spectral density of both the first and second frequency bands indicate that the sampled LFP signal is contaminated with artifacts.

Determining the probabilistic entropy value by comparing an entropy of one or more features of the bioelectrical signal to a threshold limit.

As another example, processing circuitry 210 may determine the probabilistic entropy value of the bioelectrical signal by comparing an entropy of one or more features of the bioelectrical signal to a threshold limit. For example, processing circuitry 210 uses a classification method to compare multiple features, such as the spectral entropy, threshold crossing rate values and/or inter-threshold crossing interval times, of the bioelectrical signal to one another. For example, such a classifier may categorize artifact and/or normal signal types, return the probability of an artifact in the bioelectrical signal, or provide another rating of signal quality with respect to signal regularity or lack thereof. In this example, a feature that exceeds the threshold limit may be identified as a statistical outlier in comparison to other features of the sensed bioelectrical signal. Processing circuitry 210 may determine that such statistical outliers are indicative that the bioelectrical signal may be contaminated with artifacts in several ways, which are described in more detail below.

As a first example, processing circuitry 210 may determine the probabilistic entropy value of the bioelectrical signal by analyzing a rate over time at which a feature of the bioelectrical signal exceeds a threshold limit. As an example where the one or more features of the bioelectrical signal is an amplitude of the bioelectrical signal, processing circuitry 210 may determine the probabilistic entropy value of the bioelectrical signal by analyzing a rate over time at which the amplitude of the bioelectrical signal exceeds a threshold limit. If a large number of such amplitude threshold crossings occur over a certain period of time, the bioelectrical signal may be contaminated with artifacts.

For example, processing circuitry 210 compares a determined rate at which the amplitude exceeds a threshold limit with a rate threshold for the bioelectrical signal. As one example, processing circuitry 210 determines a rate over time at which an amplitude of a first bioelectrical signal exceeds a threshold limit and a rate over time at which an amplitude of a second bioelectrical signal exceeds the threshold limit. If the rate of the first bioelectrical signal is less than the rate threshold, the rate of the first bioelectrical signal is indicative of a bioelectrical signal with no or few artifacts. Further, if the rate of the second bioelectrical signal is greater than the rate threshold, the rate of the second bioelectrical signal is indicative of a bioelectrical signal contaminated with artifacts. In some examples, the rate over time at which an amplitude of the bioelectrical signal exceeds the threshold limit may be used as an input to a machine learning system that processes one or more inputs to determine whether the inputs are indicative of the presence of artifacts in the bioelectrical signal as described above.

In some examples, the threshold limit is a first interquartile range of sensed amplitudes of the bioelectrical signal. In some examples, processing circuitry 210 determines the threshold limit as an interquartile range of a median-subtracted normalization of the bioelectrical signal. For example, processing circuitry 210 may determine the median-subtracted normalization of the bioelectrical signal by calculating a median value of the sampled amplitudes of the bioelectrical signal and subtracting the median value from the sampled amplitudes of the bioelectrical signal to, and then dividing the resulting values by the interquartile range.

As a second example, processing circuitry 210 may determine the probabilistic entropy value of the bioelectrical signal by analyzing an entropy of lengths of successive intervals between instances at which one or more features of the bioelectrical signal exceeds a signal threshold limit. As an example where the one or more features of the bioelectrical signal is an amplitude of the bioelectrical signal, processing circuitry 210 determines an interval of time between a first instance at which an amplitude of the bioelectrical signal exceeds a signal threshold limit and a second instance at which the amplitude of the bioelectrical signal exceeds the signal threshold limit. In some examples, the signal threshold limit is a first interquartile range of sensed amplitudes of the bioelectrical signal. In some examples, processing circuitry 210 determines a Shannon entropy of the set of intervals of time. For example, processing circuitry 210 may determine a time series of inter-threshold crossing intervals as described above. Processing circuitry 210 constructs a histogram of a plurality of intervals of time, wherein each interval of time is between two instances at which an amplitude of the bioelectrical signal exceeds the signal threshold limit.

Processing circuitry 210 may determine the probabilistic entropy value of the bioelectrical signal based on the resulting entropy demonstrated by the histogram of the plurality of intervals of time. For example, processing circuitry 210 compares the entropy of the intervals of time to an entropy threshold value for the bioelectrical signal. The techniques of the disclosure recognize that as the entropy increases for intervals of time between two successive instances at which an amplitude of the bioelectrical signal exceeds the threshold limit, the likelihood of the presence of artifacts in the signal decreases. Thus, if the entropy of such detected intervals is less than the entropy threshold value, the entropy is indicative of a bioelectrical signal that likely contains artifacts. Conversely, if the entropy of such detected intervals is greater than the entropy threshold value, the entropy is indicative of a bioelectrical signal that has with few or no artifacts. In some examples, processing circuitry 210 performs such an analysis of the entropy of the intervals of time between two successive threshold crossings separately for a plurality of different threshold limits (e.g., a first interquartile range of intervals of time between two instances at which an amplitude of the bioelectrical signal exceeds the threshold limit, a second interquartile range of intervals of time between two instances at which an amplitude of the bioelectrical signal exceeds the threshold limit, etc.).

As a specific example, a bioelectrical signal that contains artifacts of a periodic waveform, such as a sine wave, may cross a threshold limit at fairly regular intervals. Thus, the entropy decreases for the intervals of time that are between two successive signal crossings of the threshold limit. This decrease in signal-crossing entropy indicates a likely presence of an artifact.

In some examples, the entropy of the intervals between the first instance at which an amplitude of the bioelectrical signal exceeds a signal threshold limit and the second instance at which the amplitude of the bioelectrical signal exceeds the signal threshold limit may be used as an input to a machine learning system that processes one or more inputs to determine whether the inputs are indicative of the presence of artifacts in the bioelectrical signal as described above. In some examples, if processing circuitry 210 identifies no occurrences where an amplitude of the bioelectrical signal exceeds the threshold limit, then there is no interval of time between a first instance at which an amplitude of a bioelectrical signal exceeds a threshold limit and a second instance at which the amplitude of the bioelectrical signal exceeds the threshold limit. In such a situation, the likelihood of artifacts in the signal may be very low. Accordingly, processing circuitry 210 may assign a value of "−1" to the probabilistic entropy value of the bioelectrical signal to drive the determination by the machine learning system towards a determination that the bioelectrical signal does not include artifacts.

Determining the probabilistic entropy value using combinations of techniques.

In some examples, processing circuitry 210 may determine the probabilistic entropy value of the bioelectrical signal by combining multiple techniques for determining the probabilistic entropy value that are described above. For example, processing circuitry 210 may apply two or more of the techniques described above to one or more features of a sensed bioelectrical signal and apply different weights to each result to generate a probabilistic entropy value of the bioelectrical signal that is more accurate than the use of a single methodology alone.

For example, processing circuitry 210 may determine the probabilistic entropy value of the bioelectrical signal using a combination of any of (1) analyzing the statistical measure of randomness of spectral power across a plurality of frequency bands of the bioelectrical signal; (2) analyzing a rate over time at which an amplitude of the bioelectrical signal exceeds a signal threshold limit; or (3) analyzing an entropy of intervals of time between two successive instances at which an amplitude of the bioelectrical signal exceeds the signal threshold limit. In such example, processing circuitry 210 may determine that the bioelectrical signal is contaminated with artifacts if artifacts are indicated by only one of the aforementioned techniques, by more than one of the aforementioned techniques, or by all of the aforementioned techniques. In some examples, may apply a different weight to each of the aforementioned techniques, each weight corresponding to a strength of a correlation of the technique to the presence of artifacts in the bioelectrical signal.

In some examples, prior to determining the probabilistic entropy value of the bioelectrical signal, processing circuitry 210 may determine a normalization of the bioelectrical signal. In this example, processing circuitry 210 may subsequently determining the probabilistic entropy value of the normalized bioelectrical signal using the aforementioned techniques. By determining the normalization of the bioelectrical signal, processing circuitry 210 may allow for a unified and simplified analysis of a plurality of bioelectrical signals having a multitude of different characteristics and waveforms.

Processing circuitry 210 selects, based on the comparisons described above, a subset of electrodes 116, 118. In some examples, the subset of electrodes 116, 118 includes only those electrodes whose corresponding bioelectrical signals are determined by processing circuitry 210 to be indicative of having no or minimal artifacts. In other words, the electrodes whose corresponding bioelectrical signals are determined by processing circuitry 210 to be indicative of having artifacts are excluded from the subset. Processing circuitry 210 controls, based on the bioelectrical signals sensed via respective electrodes of the subset of electrodes 116, 118 and excluding the bioelectrical signals of the plurality of bioelectrical signals sensed via respective electrodes 116, 118 not in the subset, delivery of electrical stimulation therapy to patient 112.

In some examples, processing circuitry 210 executes a machine learning system trained as described above. In some examples, the machine learning system implements a logistic regression model, a support vector machine (SVM) model, a regression tree, a gradient boosting model, or other type of neural network model to create an artifact detector that uses probabilistic entropy values of the bioelectrical signal as determined by processing circuitry 210 as inputs. For example, the machine learning system may process the respective probabilistic entropy values of the bioelectrical signal determined by processing circuitry 210 to identify one or more electrodes that satisfy criteria of a machine learning model trained using the process described above. In some examples, the identified one or more electrodes are electrodes for which bioelectrical signals sensed via the identified one or more electrodes show no or few artifacts. In some examples, the machine learning system processes a variety of different types of probabilistic entropy values of the bioelectrical signal to identify the one or more electrodes. For example, the machine learning system may process a statistical measure of randomness of spectral power across the plurality of frequency bands of a respective bioelectrical signal sensed via an electrode, a rate at which an amplitude of the respective bioelectrical signal sensed via the electrode exceeds the amplitude threshold limit, and an entropy of intervals of time between successive instances at which an amplitude of the bioelectrical signal sensed via the electrode exceeds a threshold limit to identify the one or more electrodes. In some examples, the machine learning system may assign different weights or coefficients to the different types of probabilistic entropy values of the bioelectrical signal as determined during the training process described above. For example, the machine learning system may determine, based on the machine learning model, that the statistical measure of randomness of spectral power across the plurality of frequency bands of a bioelectrical signal should be given less weight than the rate at which an amplitude of the bioelectrical signal exceeds the amplitude threshold limit. As another example, the machine learning system may determine, based on the machine learning model, that the statistical measure of randomness of spectral power across the plurality of frequency bands of a bioelectrical signal should be given more weight than the entropy of intervals of time between successive instances at which an amplitude of the bioelectrical signal exceeds the threshold limit. Processing circuitry 210 selects the identified electrodes as the subset of electrodes 116, 118 for use in controlling delivery of therapy to patient 112.

In some examples, processing circuitry 210 transmits, via telemetry circuitry 208, an indication that an artifact is present in the electrodes excluded from the subset. In some examples, the indication causes programmer 104 to display, to a clinician or patient, a notification that an artifact is present in the electrodes excluded from the subset.

Accordingly, the techniques disclosed herein may provide enhanced accuracy in the identification of artifacts in electrodes. For example, the techniques of the disclosure may detect artifacts that may otherwise be difficult to detect using conventional artifact detection methods, such as artifacts that have variable signal amplitudes across multiple recordings. Thus, by identifying and eliminating measurements from electrodes that are contaminated with artifacts, the techniques of the disclosure may provide higher reliability in aDBS systems. For example, the techniques of the disclosure may increase the likelihood that signals sensed by the electrodes and used as biomarkers for aDBS accurately reflect the true bioelectrical signal and avoid erroneous measurements which may adversely affect the therapy provided to the patient. Therefore, the techniques disclosed herein may provide aDBS therapy to a patient that is more effective than conventional systems.

Figure 3:
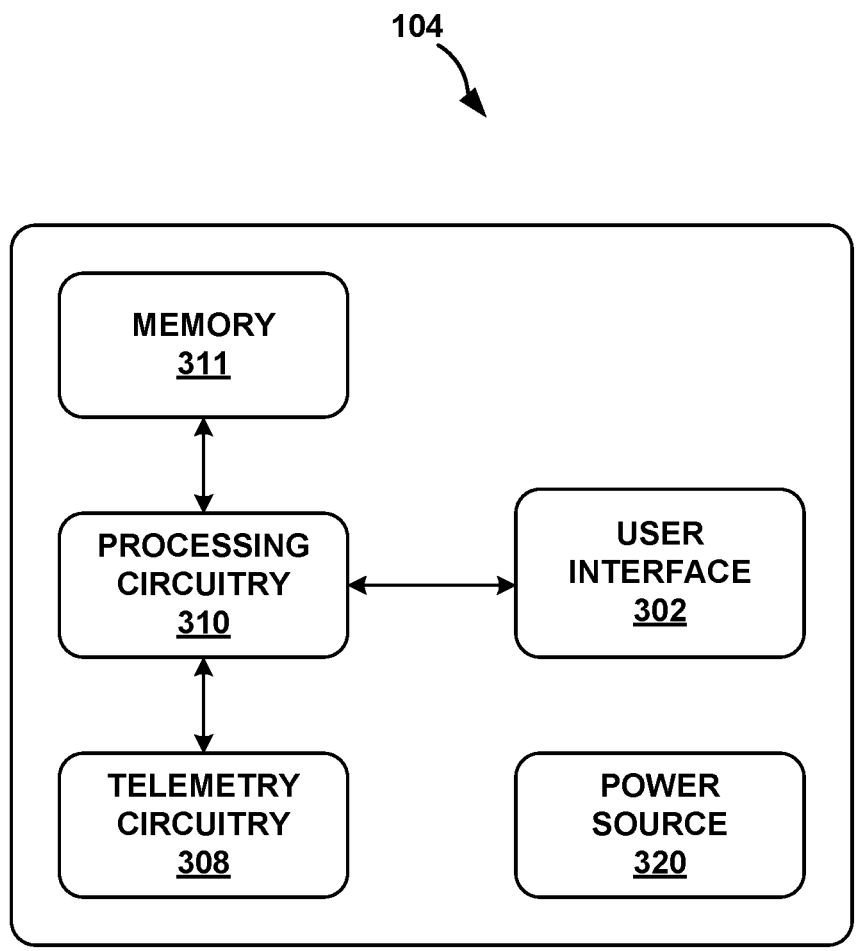
FIG. 3 is a block diagram of the external programmer of FIG. 1 for controlling delivery of adaptive DBS therapy according to an example of the techniques of the disclosure.

FIG. 3 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 311, user interface 302, telemetry circuitry 308, and power source 320. Memory 311 may store instructions that, when executed by processing circuitry 310, cause processing circuitry 310 and external programmer 104 to provide the functionality ascribed to external programmer 104 throughout this disclosure. Each of these components, or modules, may include electrical circuitry that is configured to perform some or all of the functionality described herein. For example, processing circuitry 310 may include processing circuitry configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate modules, in some examples, processing circuitry 310 and telemetry circuitry 308 may be functionally integrated with one another. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain a parameter set from memory, select a spatial electrode movement pattern, or receive a user input and send a corresponding command to IMD 104, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry circuitry 308 may support wireless communication between IMD 106 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry circuitry 308 may be configured to transmit a spatial electrode movement pattern or other stimulation parameter values to IMD 106 for delivery of stimulation therapy.

In some examples, processing circuitry 310 of external programmer 104 defines the parameters of electrical stimulation therapy, stored in memory 311, for delivering adaptive DBS to patient 112. In one example, processor 311 of external programmer 104, via telemetry circuitry 308, issues commands to IMD 106 causing IMD 106 to deliver electrical stimulation therapy via electrodes 116, 118 via leads 114.

According to the techniques of the disclosure, external programmer 104 may use the probabilistic entropy of one or more bioelectrical signals of brain 120 of patient 112 sensed via electrodes 116, 118 of IMD 106 to differentiate electrodes capable of sensing clean bioelectrical signals from electrodes contaminated with artifacts. The techniques of the disclosure recognize that neuronal LFP activity in brain 120 of patient 112 is typically a stochastic (e.g., random) process and exhibits high entropy. In contrast, the techniques of the disclosure recognize that pattern or order in a sensed bioelectrical signal (e.g., low entropy), may be indicative of artifacts in the sensed signal, such as artifacts occurring due to ECG, movement, or other periodic artifacts. In some examples, external programmer 104 may verify that a bioelectrical signal sensed by one of electrodes 116, 118 of IMD 106 is of a sufficient quality for use as a biomarker in controlling aDBS therapy. In some examples, external programmer 104 may use a probabilistic entropy of a bioelectrical signal sensed by one of recording electrodes 116, 118 as an indicator of ECG or other periodic artifacts present in recorded LFP signals of brain 120 of patient 112.

In one example, IMD 106 senses, via electrodes 116, 118, a plurality of bioelectrical signals of brain 120 of patient 112. Processing circuitry 310 receives, via telemetry circuitry 308 and from IMD 106, the plurality of bioelectrical signals of brain 120 of patient 112. Processing circuitry 310 determines, for each bioelectrical signal, a probabilistic entropy value of the bioelectrical signal. Processing circuitry 310 compares each of the respective probabilistic entropy values of the sensed bioelectrical signal to respective entropy threshold values. In some examples, processing circuitry 310 may determine the probabilistic entropy value of each bioelectrical signal and compare the probabilistic entropy to respective entropy threshold values in a similar fashion as described above with respect to processing circuitry 210 of IMF 106 of FIG. 2.

Processing circuitry 310 selects, based on the comparisons described above, a subset of electrodes 116, 118. In some examples, the subset of electrodes 116, 118 includes only those electrodes whose corresponding bioelectrical signals are determined by processing circuitry 310 to be indicative of having no or minimal artifacts. In other words, the electrodes whose corresponding bioelectrical signals are determined by processing circuitry 310 to be indicative of having artifacts are excluded from the subset. Processing circuitry 310 controls, based on the bioelectrical signals sensed via respective electrodes of the subset of electrodes 116, 118 and excluding the bioelectrical signals of the plurality of bioelectrical signals sensed via respective electrodes 116, 118 not in the subset, IMD 106 to deliver electrical stimulation therapy to patient 112. In some examples, processing circuitry 310 outputs, for display to a clinician or patient, a notification that an artifact is present in the electrodes excluded from the subset.

Figure 4:
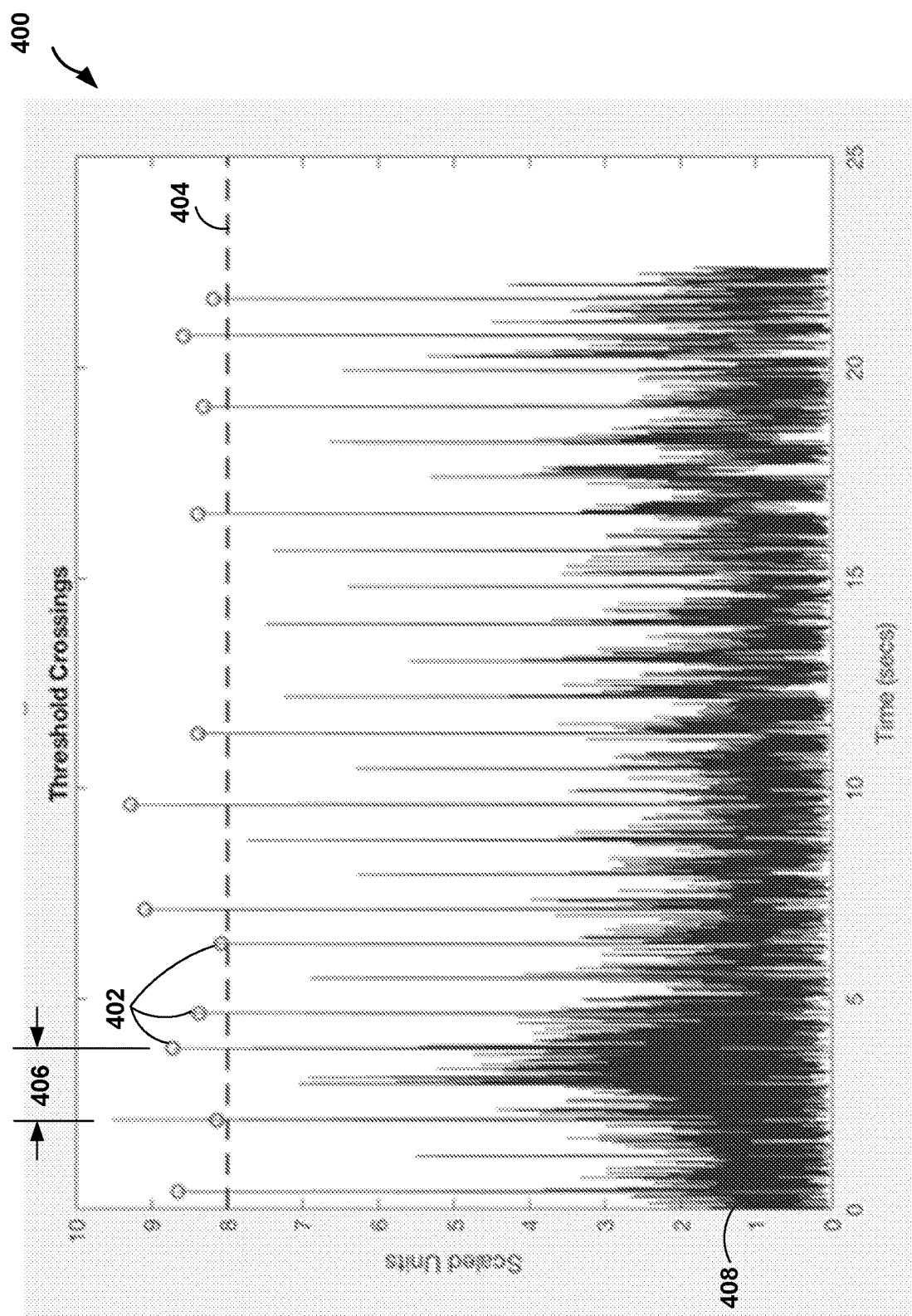
FIG. 4 is an illustration of a sensed bioelectrical signal of a patient.

FIG. 4 is an illustration of a sensed bioelectrical signal 400 of a patient. For convenience, FIG. 4 is described with respect to FIG. 1. For example, IMD 106 of FIG. 1 may sense, via one of electrodes 116, 118, bioelectrical signal 400 from brain 120 of patient 112. In one example, bioelectrical signal 400 may be a sensed LFP of brain 120 of patient 112.

In examples where bioelectrical signal 400 is an example of sensed neuronal LFP activity in brain 120 of patient 112, neuronal LFP activity is typically a stochastic (e.g., random) process and exhibits high entropy. In contrast, patterns or order (e.g., low entropy) occurring in bioelectrical signal 400 may be indicative of artifacts in the sensed signal, such as artifacts occurring due to ECG, movement, or other periodic artifacts. Accordingly, the probabilistic entropy of bioelectrical signal 400 may be used to determine whether artifacts are present in bioelectrical signal 400.

For example, FIG. 4 depicts threshold limit 404. In some examples, threshold limit 404 is a first interquartile range of sensed amplitudes of bioelectrical signal 400. In some examples, threshold limit 404 is a second interquartile range of sensed amplitudes of bioelectrical signal 400. Bioelectrical signal 400 exhibits a plurality of threshold crossings 402. Each threshold crossing 402 corresponds to an instance where an amplitude of bioelectrical signal 400 exceeds threshold limit 404. Further, interval length 406 depicts an interval of time between a first threshold crossing 402 at which the amplitude of bioelectrical signal 400 exceeds threshold limit 404 and a second threshold crossing 402 at which the amplitude of bioelectrical signal 400 exceeds threshold limit 404.

In some examples, IMD 106 may compute a rate over time at which an amplitude of bioelectrical signal 400 exceeds threshold limit 404 by computing the number of threshold crossings 402 in a period of time (e.g., 1 second, 30 seconds, 60 seconds, etc.). Further, IMD 106 compares the rate of threshold crossings 402 to a rate threshold. If the rate of threshold crossings 402 of bioelectrical signal 400 is less than the rate threshold, the rate of threshold crossings 402 may indicate that bioelectrical signal 400 has no or few artifacts. In contrast, the rate of threshold crossings 402 of bioelectrical signal 400 is greater than the rate threshold, the rate of threshold crossings 402 may indicate that bioelectrical signal 400 is contaminated with artifacts.

As another example, IMD 106 may compute interval length 406 by determining a length of time between a first threshold crossing 402 at which the amplitude of bioelectrical signal 400 exceeds threshold limit 404 and a second threshold crossing 402 at which the amplitude of bioelectrical signal 400 exceeds threshold limit 404. Further, IMD 106 compares an entropy of multiple interval lengths 406 to an entropy threshold value. If the entropy of the multiple interval lengths 406 is less than the entropy threshold value, then the entropy is indicative of a bioelectrical signal contaminated with artifacts. Further, if the entropy of the multiple interval lengths 406 is greater than the entropy threshold value, then the entropy is indicative of a bioelectrical signal with no or few artifacts.

Figure 5:
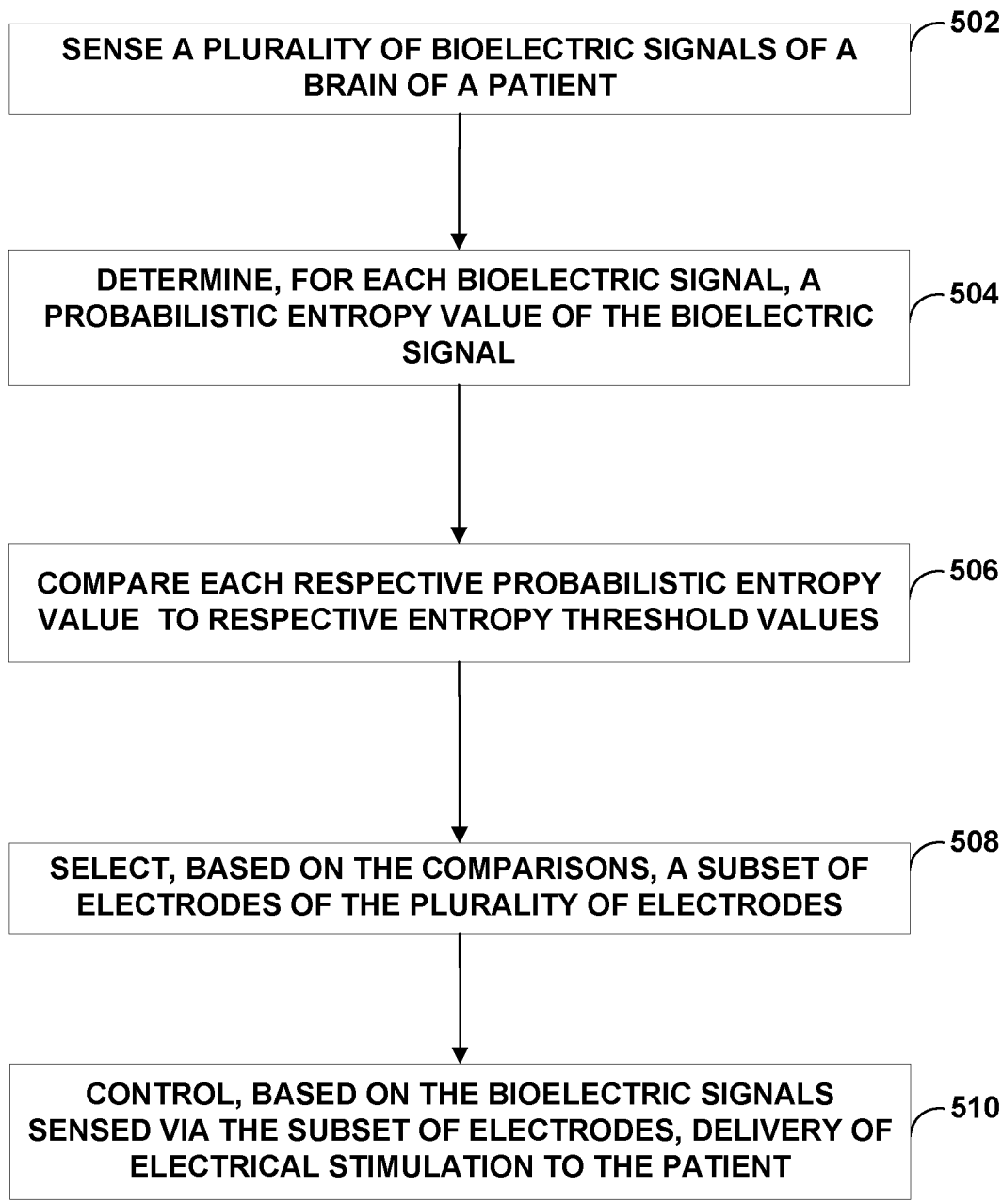
FIG. 5 is a flowchart illustrating an example operation in accordance with the techniques of the disclosure.

FIG. 5 is a flowchart illustrating an example operation in accordance with the techniques of the disclosure. For convenience, FIG. 5 is described with respect to FIG. 1. In the example operation of FIG. 5, IMD 106 uses a probabilistic entropy of a bioelectrical signal of brain 120 of patient 112 sensed via electrodes 116, 118 to differentiate electrodes capable of sensing clean bioelectrical signals from electrodes contaminated with artifacts.

In one example, IMD 106 senses, via electrodes 116, 118 and sensing circuitry 204, a plurality of bioelectrical signals of brain 120 of patient 112 (502). IMD 106 determines, for each bioelectrical signal sensed at a respective electrode 116, 118, a probabilistic entropy value of the bioelectrical signal (504). In some examples, the probabilistic entropy value of the bioelectrical signal is a probability distribution of values of the bioelectrical signal over a period of time. In some examples, the probabilistic entropy value of the bioelectrical signal is a statistical measure of randomness of values of the bioelectrical signal over a period of time. Thus, the probabilistic entropy value of the bioelectrical signal is a measure of the level of randomness of the bioelectrical signal.

IMD 106 compares each of the respective probabilistic entropy values of the sensed bioelectrical signals to respective entropy threshold values (506). IMD 106 selects, based on the comparisons, a subset of electrodes 116, 118 (508). In some examples, the subset of electrodes 116, 118 includes only those electrodes whose corresponding bioelectrical signals are determined by IMD 106 to be indicative of having no or minimal artifacts. In other words, the electrodes whose corresponding bioelectrical signals are determined by IMD 106 to be indicative of having artifacts are excluded from the subset. IMD 106 controls, based on the bioelectrical signals sensed via respective electrodes of the subset of electrodes 116, 118 and excluding the bioelectrical signals of the plurality of bioelectrical signals sensed via respective electrodes 116, 118 not in the subset, delivery of electrical stimulation therapy to patient 112 (510).

Figure 6:
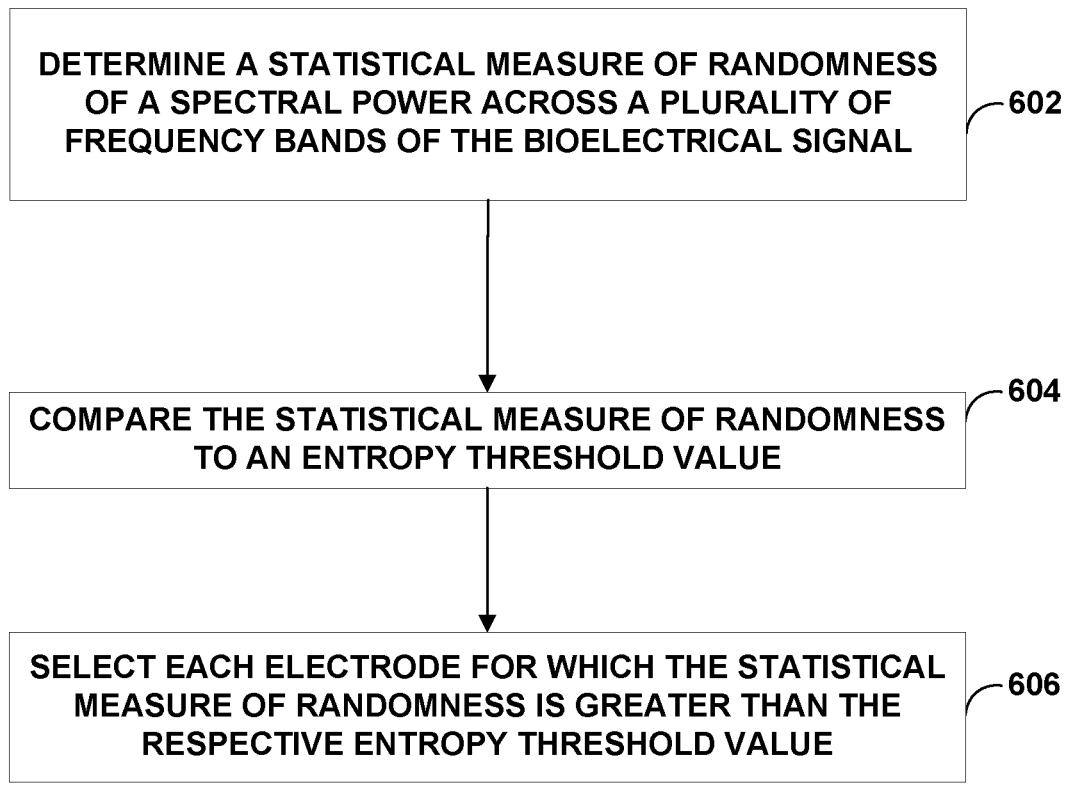
FIG. 6 is a flowchart illustrating an example operation in accordance with the techniques of the disclosure.

FIG. 6 is a flowchart illustrating an example operation in accordance with the techniques of the disclosure. For convenience, FIG. 6 is described with respect to FIG. 1. In the example operation of FIG. 6, IMD 106 determines a probabilistic entropy value of a bioelectrical signal sensed from patient 112 by analyzing a statistical measure of randomness of spectral power across a plurality of frequency bands of the bioelectrical signal.

For example, IMD 106 divides the bioelectrical signal into a plurality of frequency bands. IMD 106 determines a statistical measure of randomness of spectral power across the plurality of frequency bands (602). IMD 106 compares the statistical measure of randomness of spectral power across the plurality of frequency bands to respective entropy threshold values (604). As one example, if the statistical measure of randomness of a power of a first frequency band exceeds an entropy threshold value for the first frequency band, the statistical measure of randomness is indicative of a bioelectrical signal with no or few artifacts. As another example, if the statistical measure of randomness of a power of a second frequency band is less than an entropy threshold value for the second frequency band, the statistical measure of randomness is indicative of a bioelectrical signal contaminated with artifacts. In some examples, if one statistical measure of randomness of a power of one frequency band indicates that the bioelectrical signal is contaminated with artifacts, IMD 106 determines that the bioelectrical signal is contaminated with artifacts. In another example, IMD 106 determines that the bioelectrical signal is contaminated with artifacts only if each statistical measure of randomness of the power of each frequency band within an LFP recording indicates that the bioelectrical signal is contaminated with artifacts.

IMD 106 selects, based on the comparisons, a subset of electrodes 116, 118 (606). For example, IMD 106 selects each electrode of electrodes 116, 118 for which the statistical measure of randomness of spectral power across the plurality of frequency bands of a respective bioelectrical signal sensed via the electrode is greater than the respective entropy threshold value.

Figure 7:
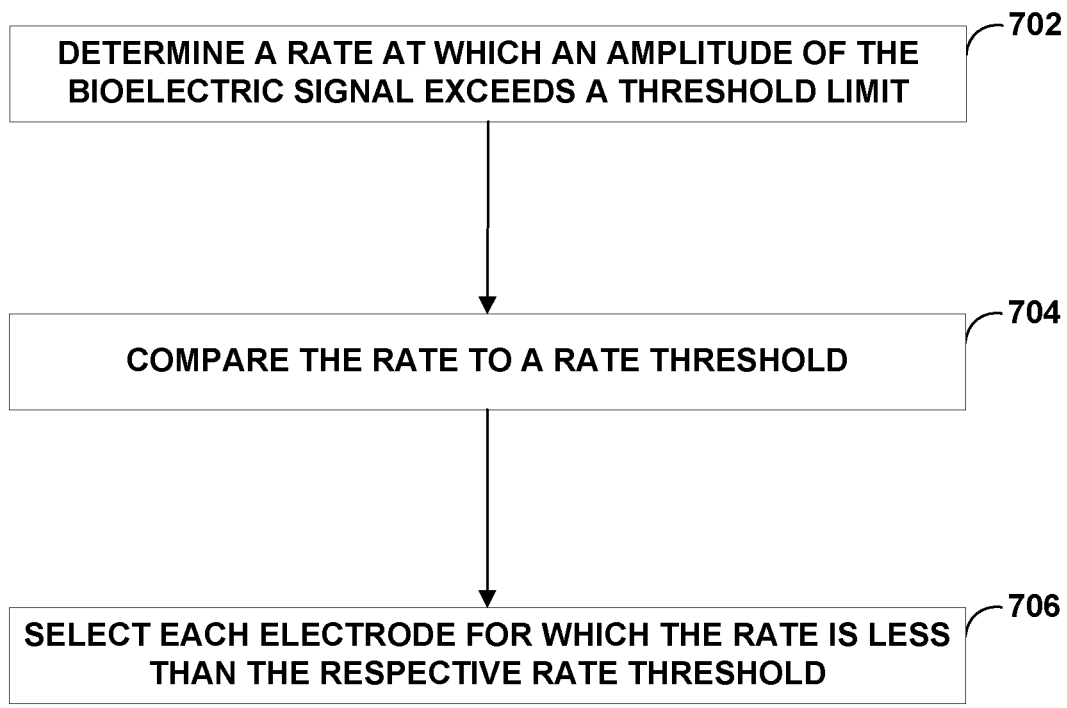
FIG. 7 is a flowchart illustrating an example operation in accordance with the techniques of the disclosure.

FIG. 7 is a flowchart illustrating an example operation in accordance with the techniques of the disclosure. For convenience, FIG. 7 is described with respect to FIG. 1. In the example operation of FIG. 7, IMD 106 determines a probabilistic entropy value of a bioelectrical signal sensed from patient 112 by analyzing a rate over time at which an amplitude of the bioelectrical signal exceeds a threshold limit.

In one example, IMD 106 determines a rate over time at which an amplitude of the bioelectrical signal exceeds a threshold limit (702). In some examples, the threshold limit is a first interquartile range of sensed amplitudes of the bioelectrical signal. IMD 106 compares the determined rate with a rate threshold for the bioelectrical signal (704). As one example, IMD 106 determines a rate over time at which an amplitude of a first bioelectrical signal exceeds a threshold limit and a rate over time at which an amplitude of a second bioelectrical signal exceeds a threshold limit. If the rate of the first bioelectrical signal is less than the rate threshold, IMD 106 determines that the rate of the first bioelectrical signal is indicative of a bioelectrical signal with no or few artifacts. Further, if the rate of the second bioelectrical signal is greater than the rate threshold, IMD 106 determines that the rate of the second bioelectrical signal is indicative of a bioelectrical signal contaminated with artifacts.

IMD 106 selects, based on the comparisons, a subset of electrodes 116, 118 (706). For example, IMD 106 selects each electrode of electrodes 116, 118 for which a rate at which an amplitude of a respective bioelectrical signal sensed via the electrode exceeds the threshold limit is less than the respective rate threshold.

Figure 8:
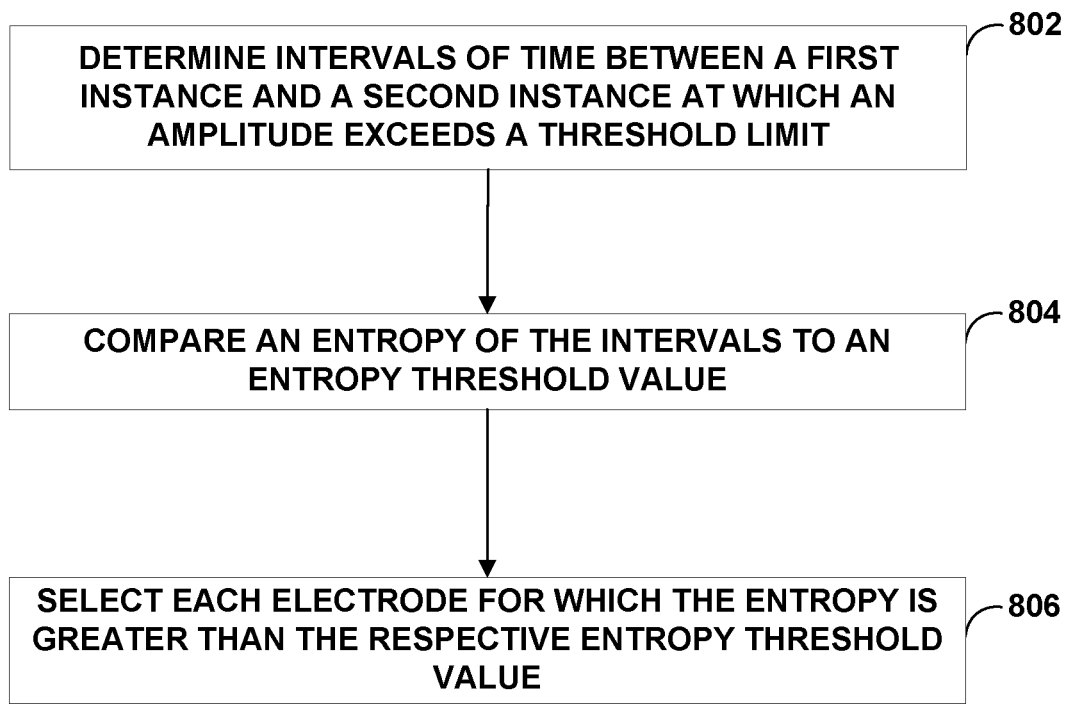
FIG. 8 is a flowchart illustrating an example operation in accordance with the techniques of the disclosure.

FIG. 8 is a flowchart illustrating an example operation in accordance with the techniques of the disclosure. For convenience, FIG. 8 is described with respect to FIG. 1. In the example operation of FIG. 8, IMD 106 determines a probabilistic entropy value of a bioelectrical signal sensed from patient 112 by analyzing an entropy of lengths of successive intervals between instances at which an amplitude of the bioelectrical signal exceeds a threshold limit.

In one example, IMD 106 determines an entropy of multiple intervals of time between a first instance at which an amplitude of the bioelectrical signal exceeds a threshold limit and a second instance at which the amplitude of the bioelectrical signal exceeds the threshold limit (802). In some examples, IMD 10 determines a Shannon entropy of the intervals of time. In some examples, the threshold limit is a first interquartile range of sensed amplitudes of the bioelectrical signal.

IMD 106 compares the entropy of the intervals of time to an entropy threshold value for the bioelectrical signal (804). For example, IMD 106 identifies intervals of time between a first instance at which an amplitude of a bioelectrical signal exceeds a threshold limit and a second instance at which the amplitude of the bioelectrical signal exceeds the threshold limit. Further, IMD 106 determines an entropy of the intervals of time between successive instances at which an amplitude of a bioelectrical signal exceeds the threshold limit. If the entropy of the intervals is less than the entropy threshold value, IMD 106 determines that the entropy of the intervals is indicative of a bioelectrical signal contaminated with artifacts. Further, if the entropy of the intervals is greater than the entropy threshold value, IMD 106 determines that the interval is indicative of a bioelectrical signal with no or few artifacts.

IMD 106 selects, based on the comparisons, a subset of electrodes 116, 118 (806). For example, IMD 106 determines, for each electrode of electrodes 116, 118, an entropy of intervals of time between successive instances at which an amplitude of a respective bioelectrical signal sensed via the electrode exceeds a signal threshold limit. IMD 106 selects each electrode of electrodes 116, 118 for which the entropy of the successive intervals is greater than the respective entropy threshold value.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   sensing, via a plurality of electrodes, a plurality of bioelectrical signals of a brain of a patient;
   determining, by processing circuitry and for each bioelectrical signal of the plurality of bioelectrical signals sensed at a respective electrode of the plurality of electrodes, a probabilistic entropy value of the bioelectrical signal;
   comparing, by the processing circuitry, each of the respective probabilistic entropy values of the bioelectrical signal to respective entropy threshold values; and
   selecting, by the processing circuitry and based on the comparisons, a subset of electrodes of the plurality of electrodes by:
      including, in the subset, at least one electrode of the plurality of electrodes for which the comparison of the probabilistic entropy value of the bioelectrical signal sensed via the at least one electrode to the respective entropy threshold value is indicative that the bioelectrical signal exhibits high entropy; and
      excluding, from the subset, each electrode of the plurality of electrodes for which the comparison of the probabilistic entropy value of the bioelectrical signal sensed via the electrode to the respective entropy threshold value is indicative that the bioelectrical signal exhibits low entropy; and
   controlling, by the processing circuitry and based on the bioelectrical signals of the plurality of bioelectrical signals sensed via respective electrodes of the subset of electrodes and excluding the bioelectrical signals of the plurality of bioelectrical signals sensed via respective electrodes not in the subset of electrodes, delivery of electrical stimulation therapy to the patient via at least one of the plurality of electrodes.

2. The method of claim 1,
   wherein determining, for each bioelectrical signal, the probabilistic entropy value comprises determining, for each bioelectrical signal, a probability distribution of entropy of the bioelectrical signal over a period of time,
   wherein signal components of the bioelectrical signal that have periodic behavior indicate reduced entropy, and
   wherein signal components of the bioelectrical signal that have no periodic behavior indicate increased entropy.

3. The method of claim 1, wherein determining, for each bioelectrical signal, the probabilistic entropy value comprises:
   determining that one or more signal components of a first bioelectrical signal of the plurality of bioelectrical signals demonstrate periodic behavior;
   in response to determining that the one or more signal components of the first bioelectrical signal demonstrate periodic behavior, determining a first probabilistic entropy value for the first bioelectrical signal;
   determining that one or more signal components of a second bioelectrical signal of the plurality of bioelectrical signals demonstrate aperiodic behavior; and
   in response to determining that the one or more signal components of the second bioelectrical signal demonstrate aperiodic, determining a second probabilistic entropy value for the second bioelectrical signal, wherein the first probabilistic entropy value is indicative of entropy in the first bioelectrical signal and the second probabilistic entropy value is indicative of entropy in the second bioelectrical signal, and wherein the first probabilistic entropy value and the second probabilistic entropy value indicate that the first bioelectrical signal demonstrates less entropy than the second bioelectrical signal.

4. The method of claim 1, wherein determining, for each bioelectrical signal, the probabilistic entropy value comprises determining, for each bioelectrical signal, a statistical measure of randomness over a period of time.

5. The method of claim 4,
wherein determining, for each bioelectrical signal, the statistical measure of randomness comprises determining a statistical measure of randomness of spectral power across a plurality of frequency bands of the bioelectrical signal,
wherein comparing each of the respective probabilistic entropy values of the bioelectrical signal to respective entropy threshold values comprises comparing each statistical measure of randomness of spectral power across the plurality of frequency bands of the bioelectrical signal to an entropy threshold value,
wherein including, in the subset, comprises including, in the subset, at least one electrode of the plurality of electrodes for which the statistical measure of randomness of spectral power across the plurality of frequency bands of a respective bioelectrical signal sensed via the electrode is greater than the respective entropy threshold value, and
wherein excluding, form the subset, comprises excluding, from the subset, each electrode of the plurality of electrodes for which the statistical measure of randomness of spectral power across the plurality of frequency bands of a respective bioelectrical signal sensed via the electrode is less than or equal to the respective entropy threshold value.

6. The method of claim 1,
wherein comparing each of the respective probabilistic entropy values of the bioelectrical signal to respective entropy threshold values comprises:
determining a rate at which an amplitude of each bioelectrical signal exceeds a threshold limit; and
comparing the rate at which the amplitude of the bioelectrical signal exceeds the threshold limit to a respective rate threshold,
wherein including, in the subset, comprises including, in the subset, at least one electrode of the plurality of electrodes for which a rate at which an amplitude of a respective bioelectrical signal sensed via the electrode exceeds the threshold limit is less than the respective rate threshold; and
wherein excluding, from the subset, comprises excluding, from the subset, each electrode of the plurality of electrodes for which a rate at which an amplitude of a respective bioelectrical signal sensed via the electrode exceeds the threshold limit is greater than or equal to the respective rate threshold.

7. The method of claim 6, wherein each threshold limit is an interquartile range of sensed amplitudes of a respective bioelectrical signal.

8. The method of claim 1,
wherein comparing each of the respective probabilistic entropy values of the bioelectrical signal to respective entropy threshold values comprises:

determining an entropy of intervals of time between instances at which an amplitude of the bioelectrical signal exceeds a threshold limit; and
comparing the entropy of the intervals of time to the respective entropy threshold value,
wherein including, in the subset, comprises including, in the subset, at least one electrode of the plurality of electrodes for which the entropy of the intervals of time is greater than the respective entropy threshold value, and
wherein excluding, form the subset, comprises excluding, from the subset, each electrode of the plurality of electrodes for which the entropy of the intervals of time is less than or equal to the respective entropy threshold value.

9. The method of claim 8, wherein each threshold limit is a first interquartile range of sensed amplitudes of a respective bioelectrical signal.

10. The method of claim 8, wherein determining the interval of time comprises determining a Shannon entropy of the intervals of time.

11. The method of claim 1,
wherein comparing each of the respective probabilistic entropy values of the bioelectrical signal to respective entropy threshold values comprises:
determining a statistical measure of randomness of spectral power across a plurality of frequency bands of each bioelectrical signal;
comparing the statistical measures of randomness of spectral power across the plurality of frequency bands of the bioelectrical signal to a first entropy threshold value;
determining a rate at which an amplitude of the bioelectrical signal exceeds an amplitude threshold limit;
comparing the rate at which the amplitude of the bioelectrical signal exceeds the amplitude threshold limit to a rate threshold;
determining an entropy of intervals of time between instances at which an amplitude of the bioelectrical signal exceeds a threshold limit;
comparing the entropy of the intervals of time to a second entropy threshold value, and
wherein selecting, based on the comparisons, the subset of electrodes of the plurality of electrodes comprises selecting each electrode of the subset of electrodes of the plurality of electrodes based on the statistical measure of randomness of spectral power across the plurality of frequency bands of a respective bioelectrical signal sensed via the electrode, the rate at which an amplitude of the respective bioelectrical signal sensed via the electrode exceeds the amplitude threshold limit, and the entropy of intervals of time between instances at which an amplitude of the bioelectrical signal sensed via the electrode exceeds a threshold limit.

12. The method of claim 11,
wherein comparing each of the respective probabilistic entropy values of the bioelectrical signal to respective entropy threshold values and selecting, based on the comparisons, the subset of electrodes of the plurality of electrodes further comprises processing, by a machine learning system executing on the processing circuitry, the statistical measure of randomness of spectral power across the plurality of frequency bands of a respective bioelectrical signal sensed via the electrode, the rate at which an amplitude of the respective bioelectrical signal sensed via the electrode exceeds the amplitude threshold limit, and the entropy of intervals of time between instances at which an amplitude of the bioelectrical signal sensed via the electrode exceeds the threshold limit to identify one or more electrodes of the plurality of electrodes, and wherein including, in the subset, comprises including, in the subset, the identified one or more electrodes, and wherein excluding, from the subset, comprises excluding, from the subset, each electrode of the plurality of electrodes not identified by the machine learning system.

13. The method of claim 1, wherein comparing each of the respective probabilistic entropy values of the bioelectrical signal to respective entropy threshold values and selecting, based on the comparisons, the subset of electrodes of the plurality of electrodes comprises processing, by a machine learning system executing on the processing circuitry, each of the respective probabilistic entropy values of the bioelectrical signal to identify one or more electrodes of the plurality of electrodes, and wherein including, in the subset, comprises including, in the subset, the identified one or more electrodes, and wherein excluding, from the subset, comprises excluding, from the subset, each electrode of the plurality of electrodes not identified by the machine learning system.

14. The method of claim 1, wherein comparing each of the respective probabilistic entropy values of the bioelectrical signal to respective entropy threshold values comprises:
determining a normalization of each bioelectrical signal; and
comparing a probabilistic entropy of the normalization of the bioelectrical signal to the respective entropy threshold value.

15. The method of claim 1, further comprising:
for each electrode not in the subset of electrodes, outputting, by the processing circuitry, an indication that an artifact is present in a respective bioelectrical signal sensed via the electrode.

16. The method of claim 1, wherein comparing each of the respective probabilistic entropy values of the bioelectrical signal to respective entropy threshold values comprises comparing each of the respective probabilistic entropy values of the bioelectrical signal to respective entropy threshold values to identify each electrode of the plurality of electrodes for which the bioelectrical signal sensed via the electrode is contaminated with artifacts, and wherein a comparison indicative that the bioelectrical signal exhibits low entropy is indicative of the presence of artifacts in the bioelectrical signal sensed via the electrode.

17. An implantable medical device comprising:
sensing circuitry configured to sense, via a plurality of electrodes, a plurality of bioelectrical signals of a brain of a patient; and
processing circuitry configured to:
determine, for each bioelectrical signal of the plurality of bioelectrical signals sensed at a respective electrode of the plurality of electrodes, a probabilistic entropy value of the bioelectrical signal;
compare each of the respective probabilistic entropy values of the bioelectrical signal to respective entropy threshold values;
select, based on the comparisons, a subset of electrodes of the plurality of electrodes by:

including, in the subset, at least one electrode of the plurality of electrodes for which the comparison of the probabilistic entropy value of the bioelectrical signal sensed via the at least one electrode to the respective entropy threshold value is indicative that the bioelectrical signal exhibits high entropy; and excluding, from the subset, each electrode of the plurality of electrodes for which the comparison of the probabilistic entropy value of the bioelectrical signal sensed via the electrode to the respective entropy threshold value is indicative that the bioelectrical signal exhibits low entropy; and control, based on the bioelectrical signals of the plurality of bioelectrical signals sensed via respective electrodes of the subset of electrodes and excluding the bioelectrical signals of the plurality of bioelectrical signals sensed via respective electrodes not in the subset of electrodes, delivery of electrical stimulation therapy to the patient via at least one of the plurality of electrodes.

18. The implantable medical device of claim 17,
wherein, to determine the probabilistic entropy value of the bioelectrical signal, the processing circuitry is further configured to determine a probability distribution of entropy of the bioelectrical signal over a period of time,
wherein signal components of the bioelectrical signal that have periodic behavior indicate reduced entropy, and
wherein signal components of the bioelectrical signal that have no periodic behavior indicate increased entropy.

19. The implantable medical device of claim 17, wherein, to determine, for each bioelectrical signal, the probabilistic entropy value, the processing circuitry is further configured to:
determine that one or more signal components of a first bioelectrical signal of the plurality of bioelectrical signals demonstrate periodic behavior;
in response to determining that the one or more signal components of the first bioelectrical signal demonstrate periodic behavior, determine a first probabilistic entropy value for the first bioelectrical signal;
determine that one or more signal components of a second bioelectrical signal of the plurality of bioelectrical signals demonstrate aperiodic behavior; and
in response to determining that the one or more signal components of the second bioelectrical signal demonstrate aperiodic behavior, determine a second probabilistic entropy value for the second bioelectrical signal,
wherein the first probabilistic entropy value is indicative of entropy in the first bioelectrical signal and the second probabilistic entropy value is indicative of entropy in the second bioelectrical signal, and
wherein the first probabilistic entropy value and the second probabilistic entropy value indicate that the first bioelectrical signal demonstrates less entropy than the second bioelectrical signal.

20. The implantable medical device of claim 17, wherein, to determine the probabilistic entropy value of the bioelectrical signal, the processing circuitry is further configured to determine a statistical measure of randomness over a period of time.

21. The implantable medical device of claim 20,
wherein to determine the probabilistic entropy value of the bioelectrical signal, the processing circuitry is further configured to determine a statistical measure of randomness of spectral power across a plurality of frequency bands of the bioelectrical signal, wherein, to compare each of the respective probabilistic entropy values of the bioelectrical signal to respective entropy threshold values, the processing circuitry is further configured to compare each statistical measure of randomness of spectral power across the plurality of frequency bands of the bioelectrical signal to an entropy threshold value, and wherein, to select, based on the comparisons, a subset of electrodes of the plurality of electrodes, the processing circuitry is further configured to:
- include, in the subset, at least one electrode of the plurality of electrodes for which the statistical measure of randomness of spectral power across the plurality of frequency bands of a respective bioelectrical signal sensed via the electrode is greater than the respective entropy threshold value; and
- exclude, from the subset, each electrode of the plurality of electrodes for which the statistical measure of randomness of spectral power across the plurality of frequency bands of a respective bioelectrical signal sensed via the electrode is less than or equal to the respective entropy threshold value.

22. The implantable medical device of claim 17, wherein, to compare each of the respective probabilistic entropy values of the bioelectrical signal to respective entropy threshold values, the processing circuitry is further configured to:
- determine a rate at which an amplitude of each bioelectrical signal exceeds a threshold limit; and
- compare the rate at which the amplitude of the bioelectrical signal exceeds the threshold limit to a respective rate threshold; and wherein, to select, based on the comparisons, a subset of electrodes of the plurality of electrodes, the processing circuitry is further configured to:

include, in the subset, at least one each electrode of the plurality of electrodes for which a rate at which an amplitude of a respective bioelectrical signal sensed via the electrode exceeds the threshold limit is less than the respective rate threshold; and exclude, from the subset, each electrode of the plurality of electrodes for which a rate at which an amplitude of a respective bioelectrical signal sensed via the electrode exceeds the threshold limit is greater than or equal to the respective rate threshold.

23. The implantable medical device of claim 17, wherein, to compare each of the respective probabilistic entropy values of the bioelectrical signal to respective entropy threshold values, the processing circuitry is further configured to:
- determine an entropy of intervals of time between instances at which an amplitude of the bioelectrical signal exceeds a threshold limit; and
- compare the entropy of the intervals of time to the respective entropy threshold value, and wherein, to select, based on the comparisons, a subset of electrodes of the plurality of electrodes, the processing circuitry is further configured to:
- include, in the subset, at least one electrode of the plurality of electrodes for which the entropy of the intervals of time is greater than the respective entropy threshold value; and
- exclude, from the subset, each electrode of the plurality of electrodes for which the entropy of the intervals of time is less than or equal to the respective entropy threshold value.

24. A system comprising:

a plurality of electrodes;

an implantable medical device comprising:
- sensing circuitry configured to sense, via the plurality of electrodes, a plurality of bioelectrical signals of a brain of a patient; and processing circuitry configured to:
- determine, for each bioelectrical signal of the plurality of bioelectrical signals sensed at a respective electrode of the plurality of electrodes, a probabilistic entropy value of the bioelectrical signal;
- compare each of the respective probabilistic entropy values of the bioelectrical signal to respective entropy threshold values;
- select, based on the comparisons, a subset of electrodes of the plurality of electrodes by:
  - including, in the subset, at least one electrode of the plurality of electrodes for which the comparison of the probabilistic entropy value of the bioelectrical signal sensed via the at least one electrode to the respective entropy threshold value is indicative that the bioelectrical signal exhibits high entropy; and
  - excluding, from the subset, each electrode of the plurality of electrodes for which the comparison of the probabilistic entropy value of the bioelectrical signal sensed via the electrode to the respective entropy threshold value is indicative that the bioelectrical signal exhibits low entropy; and
- control, based on the bioelectrical signals of the plurality of bioelectrical signals sensed via respective electrodes of the subset of electrodes and excluding the bioelectrical signals of the plurality of bioelectrical signals sensed via respective electrodes not in the subset of electrodes, delivery of electrical stimulation therapy to the patient via at least one of the plurality of electrodes.

25. The system of claim 24, wherein the implantable medical device comprises the processing circuitry.

26. The system of claim 24, further comprising an external device, wherein the external device comprises the processing circuitry.

* * * * *